United States Patent [19]

Krapcho et al.

[11] 4,174,317
[45] Nov. 13, 1979

[54] 3,3-DICHLORO-2-AZETIDINONE DERIVATIVES

[75] Inventors: John Krapcho, Somerset; Chester F. Turk, Kendall Park, both of N.J.

[73] Assignee: E. R. Squibb & Sons, Inc., Princeton, N.J.

[21] Appl. No.: 892,361

[22] Filed: Mar. 24, 1978

[51] Int. Cl.² .................. C07D 205/08; C07D 401/06; C07D 403/06; C07D 405/06
[52] U.S. Cl. ................ 260/239 A; 542/414; 542/424; 542/425; 260/326.43; 260/340.5 R; 260/570.5 R; 544/111; 544/359
[58] Field of Search .................. 260/239 AL, 326.43, 260/340.5 R, 239 A; 544/111, 359; 546/208

[56] References Cited

U.S. PATENT DOCUMENTS 4,064,120  12/1977  Krapcho ........................ 260/239 A

OTHER PUBLICATIONS

Bentley et al, J. Chem. Soc., Perkins I, 1976, pp. 1725–1734, (1976).

*Primary Examiner*—Mark L. Berch
*Attorney, Agent, or Firm*—Lawrence S. Levinson; Donald J. Barrack

[57] ABSTRACT

Compounds having the formula

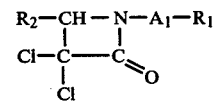

wherein $A_1$ is an alkylene group having 2 to 4 carbon atoms; $R_1$ is dialkylamino or a nitrogen containing heterocyclic group and $R_2$ is phenyl, substituted phenyl, naphthyl, or 1,3-benzodioxol-5-yl; have antiinflammatory activity.

19 Claims, No Drawings

3,3-DICHLORO-2-AZETIDINONE DERIVATIVES

RELATED APPLICATION

Copending U.S. patent application Ser. No. 803,827, now U.S. Pat. No. 4,115,382 filed June 6, 1977 discloses antiinflammatory compounds having the formula

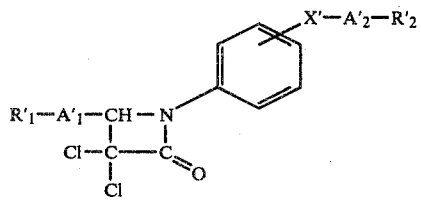

wherein X' is oxygen or sulfur; $R'_1$ is alkyl, cycloalkyl or aryl; $R'_2$ is dialkylamino or a nitrogen containing heterocyclic group; $A'_1$ is a saturated bond or an alkylene group having 1 to 4 carbon atoms; and $A'_2$ is an alkylene group having 2 to 5 carbon atoms.

BACKGROUND OF THE INVENTION

Sekiya and Morimoto, Chem. Pharm. Bull., 23, 2353 (1975) disclose that the reaction of trichloroacetic anhydride with Schiff bases yields 3,3-dichloro-2-azetidinones.

U.S. Pat. No. 4,064,120, issued Dec. 20, 1977 discloses antiinflammatory compounds having the formula

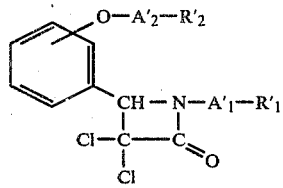

wherein the symbols are as defined above under the heading "Related Application".

SUMMARY OF THE INVENTION

Compounds having the formula

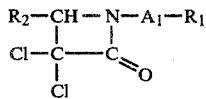

or a pharmaceutically acceptable salt thereof, have useful antiinflammatory activity. In formula I, and throughout the specification, the symbols are as defined below.

$R_1$ is dialkylamino, 1-pyrrolidinyl, 1-piperidinyl, 4-morpholinyl, 1-piperazinyl, or 4-alkyl-1-piperazinyl.

$R_2$ is phenyl, phenyl monosubstituted with an alkyl, trifluoromethyl or nitro group, phenyl mono-, di- or trisubstituted with halogen or alkoxy groups, 1-naphthyl, 2-naphthyl, or 1,3-benzodioxol-5-yl; and $A_1$ is an alkylene group having 2 to 4 carbon atoms.

The terms "alkyl" and "alkoxy", as used throughout the specification, whether alone or as part of a larger group, refer to groups having 1 to 6 carbon atoms.

The term "halogen", as used throughout the specification, refers to fluorine, chlorine, bromine or iodine.

The term "alkylene", as used throughout the specification, refers to a straight or branched chain divalent, saturated hydrocarbon group.

DETAILED DESCRIPTION OF THE INVENTION

The compounds of this invention can be prepared using as starting materials an aldehyde having the formula

and an amine having the formula $$H_2N-A_1-R_1 \qquad III$$

Reaction of an aldehyde of formula II with an amine of formula III yields the corresponding Schiff base having the formula

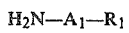

The reaction can be run in an organic solvent, e.g., an aromatic hydrocarbon such as benzene or toluene, and will preferably be run at the reflux temperature of the solvent.

Reaction of a Schiff base of formula IV with trichloroacetic anhydride, in accordance with the procedure set forth by Sekiya and Morimoto, Chem. Pharm. Bull., 23, 2353 (1975), yields the corresponding 3,3-dichloro-2-azetidinone of formula I.

The pharmaceutically acceptable salts of the compounds of formula I are readily prepared using procedures well known in the art. Acid-addition salts are specifically contemplated. Exemplary salts are the hydrohalides, sulfate, nitrate, phosphate, oxalate, tartrate, maleate, citrate, benzenesulfonate, and others.

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 grams per 70 kilograms of animal body weight per day.

The following examples are specific embodiments of this invention.

EXAMPLE 1

3,3-Dichloro-1-[3-(dimethylamino)propyl]-4-phenyl-2-azetidinone, hydrochloride (1:1)

(A) N'-Benzylidene-N,N-dimethylpropanediamine

A solution of 102.0 g of N,N-dimethylaminopropylamine in 150 ml. of benzene is treated with a solution of 101 ml. of freshly distilled benzaldehyde in 150 ml. of benzene. This mixture is stirred and refluxed for 2 hours while collecting an aqueous layer in a Dean-Stark tube. The solvent is then distilled and the residue fractionated to give 159 g of distillate, boiling point 95°–98° C. at 1 mm. of Hg.

(B)

3,3-Dichloro-1-[3-(dimethylamino)propyl]-4-phenyl-2-azetidinone, hydrochloride (1:1)

A stirred solution of 8.0 g of N'-benzylidene-N,N-dimethylpropanediamine in 50 ml. of xylene is cooled to 15°–20° C. and treated portionwise with a solution of 18.0 g of trichloroacetic anhydride in 30 ml. of xylene. The resulting solution is gradually heated. Evolution of carbon dioxide begins at about 60°–65° C. and becomes vigorous at 70°–75° C. On continued heating the mixture becomes quite dark as a solid separates and makes stirring difficult. The heating mantle is removed and the mixture is heated on a steam bath for 10 minutes at 90° C. At this point carbon dioxide evolution has essentially ceased and the cooled mixture is poured onto 300 ml. of ice-water, treated with 20 g of potassium carbonate and extracted with 200 ml. of ether (three times). The ether phases are combined and extracted with a cold solution of 5 ml. of concentrated hydrochloric acid in 100 ml. of water and then with 50 ml. of water. The aqueous phases are combined, treated portionwise with 10 g of potassium carbonate and the mixture is extracted with 100 ml. of ether (three times). The ether phases are combined, dried over magnesium sulfate, filtered, and the solvent evaporated to give 9.2 g of oily base.

The base is dissolved in dichloromethane, treated with 5 ml. of 6.1 N alcoholic hydrogen chloride, and the solvents removed on a rotary evaporator. The glass-like residue is taken up in 50 ml. of warm acetonitrile and diluted with 100 ml. of ether. On seeding and rubbing, the crystalline hydrogen chloride salt rapidly separates. After cooling for about 16 hours, the material is filtered under nitrogen, washed with ether, and dried in vacuo to yield 7.7 g of material, melting point 164°–166° C. Crystallization from 35 ml. of warm acetonitrile-70 ml. of ethyl acetate, yields 5.9 g of the title compound, melting point 165°–167° C.

EXAMPLE 2

3,3-Dichloro-1-[2-(dimethylamino)ethyl]-4-phenyl-2-azetidinone, hydrochloride (1:1)

(A) N'-Benzylidene-N,N-dimethylethylenediamine

A solution of 88.0 g of N,N-dimethylethylenediamine in 150 ml. of benzene is treated with a solution of 106 g of freshly distilled benzaldehyde in 150 ml. of benzene. This mixture is stirred and refluxed for 2 hours while collecting 22 ml. of an aqueous layer in a Dean-Stark tube. The solvent is then distilled and the residue fractionated to give 156 g of distillate, boiling point 98°–100° C. at 4 mm. of Hg.

(B)

3,3-Dichloro-1-[2-(dimethylamino)ethyl]-4-phenyl-2-azetidinone, hydrochloride (1:1)

Eight grams of N'-benzylidene-N,N-dimethylethylenediamine and 19 g of trichloroacetic anhydride are reacted in 80 ml. of xylene following the procedure described in Example 1. A fairly vigorous reaction begins at 60°–65° C; final heating is for 0.5 hours on a steam bath. An appreciable amount of tarry material is encountered during the work-up. The crude oily base (5.4 g) is dissolved in dichloromethane, treated with 1 equivalent of alcoholic hydrogen chloride and the solvents are removed on a rotary evaporator. When the glass-like residue is rubbed under 30 ml. of acetonitrile, the crystalline hydrogen chloride salt separates. Precipitation is completed by adding ether and cooling for about 16 hours. The solid is filtered under nitrogen, washed with ether, and dried in vacuo to yield 5.6 g of material, melting point 187°–189° C. Crystallization from 25 ml. of hot acetonitrile -50 ml. of ethyl acetate gives 3.8 g of material, melting point 198°–200° C. Following recrystallization from 12 ml. of acetonitrile, the product weighs 2.8 g, melting point 205°–207° C. (sintering at 203° C.).

EXAMPLE 3

3,3-Dichloro-1-[3-(4-morpholinyl)propyl]-4-phenyl-2-azetidinone, hydrochloride (1:1)

(A) N-Benzylidene-4-(3-aminopropyl)morpholine

Interaction of 50 g of N-(3-aminopropyl)morpholine and 37 g of benzaldehyde in 120 ml. of benzene according to the procedure described in Example 1 yields 70.0 g of product as an oil, boiling point 142°–147° C. at 0.1–0.2 mm. of Hg.

(B)

3,3-Dichloro-1-[3-(4-morpholinyl)propyl]-4-phenyl-2-azetidinone, hydrochloride

N-Benzylidene-4-(3-aminopropyl)morpholine (15 g) and 28 g of trichloroacetic anhydride are reacted in 115 ml. of xylene following the procedure described in Example 1. (Final heating is for 0.5 hours on a steam bath) to give 19 g of crude base as an oil. The base (18.6 g) is dissolved in dichloromethane, treated with 10 ml. of 5.5 N alcoholic hydrogen chloride, and the solvents are removed on a rotary evaporator to give a foamy residue. The residue is taken up in 50 ml. of acetonitrile and diluted to 200 ml. with ether. On seeding and rubbing, the crystalline hydrogen chloride salt separates yielding, after cooling for 3 days, 14.3 g of material, melting point 156°–158° C. (sintering at 145° C.). Crystallization from 50 ml. of hot acetonitrile-100 ml. of ethyl acetate gives 11.7 g of product as a solvate with ethyl acetate, melting point 161°–163° C. (sintering at 159° C.). To remove the ethyl acetate, the material (11.1 g) is stirred with 30 ml. of boiling methyl ethyl ketone and cooled. The final yield of the title compound is 9.1 g, melting point 163°–165° C.

EXAMPLE 4

3,3-Dichloro-1-[2-(4-morpholinyl)ethyl]-4-phenyl-2-azetidinone, hydrochloride (1:1)

(A) N-Benzylidene-4-(2-aminoethyl)morpholine

Interaction of 83.5 g of N-(2-aminoethyl)morpholine and 68 g of freshly distilled benzaldehyde in benzene according to the procedure described in Example 1 yields 135.3 g of product as a liquid, boiling point 118°–123° C. at 0.1 mm. of Hg.

(B)

3,3-Dichloro-1-[2-(4-morpholinyl)ethyl]-4-phenyl-2-azetidinone, hydrochloride (1:1)

Ten grams of N-benzylidene-4-(2-aminoethyl)morpholine and 19.5 g of trichloroacetic anhydride are reacted in 80 ml. of xylene as described in Example 1. On adding the anhydride solution a voluminous solid separates, making stirring very difficult. After heating on a steam bath for 0.5 hours and working up as in Example 1, there is obtained 10.3 g of almost completely solid crude base. Crystallization (of 10.1 g) from a mixture of 50 ml. of benzene and 150 ml. of hexane (filtering off some dark tarry material which initially separates when a portion of the hexane is added) yields 7.1 g of crystalline base in 2 crops (6.5 g and 0.6 g), melting point 85°–87° C. (sintering at 82° C.).

The base (6.8 g) is dissolved in 30 ml. of acetonitrile, cooled, treated with 3.8 ml. of 5.6 N alcoholic hydrogen chloride, and diluted to about 150 ml. with ether. On seeding and rubbing, the crystalline hydrochloride salt rapidly separates, yielding after cooling for about 16 hours 6.7 g of material, melting point 190°–192° C. Following recrystallization from 30 ml. of hot acetonitrile-70 ml. ethyl acetate, the title compound weighs 5.3 g, melting point 190°–192° C.

EXAMPLE 5

3,3-Dichloro-1-[3-(dimethylamino)propyl]-4-(2-methoxyphenyl)-2-azetidinone, hydrochloride (1:1)

(A)

N,N-Dimethyl-N'-(2-methoxybenzylidene)propanediamine

Thirty grams of o-anisaldehyde and 23 g of 3-dimethylaminopropylamine are reacted in 160 ml of benzene as described in Example 1 to give 45.8 g of oily product, boiling point 145°–148° C. at 1 mm. of Hg.

(B)

3,3-Dichloro-1-[3-(dimethylaminopropyl]-4-(2-methoxyphenyl)-2-azetidinone, hydrochloride N,N-Dimethyl-N'-(2-methoxybenzylidene)-propanediamine and 21 g of trichloroacetic anhydride are reacted in 95 ml of xylene as described in Example 1. (Final heating is for 20 minutes on steam bath) to give 13.5 g of oily base. The hydrochloride salt (prepared in dichloromethane, evaporated, and the syrupy residue crystallized from 60 ml. acetonitrile-100 ml. ether) weighs 12.5 g, melting point 162°–164° C. Following recrystallization from 60 ml. of hot acetonitrile-120 ml. ethyl acetate, the solid weighs 9.8 g, melting point 164°–166° C.

EXAMPLE 6

3,3-Dichloro-1-[3-(dimethylamino)propyl]-4-(3,4,5-trimethoxyphenyl)-2-azetidinone, hydrochloride (1:1)

N,N-Dimethyl-N'-[(3,4,5-trimethoxyphenyl)methylene]-1,3-propanediamine

Interaction of 21 g of 3,4,5-trimethoxybenzaldehyde with 11 g of 3-dimethylaminopropylamine in 80 ml. of benzene following the procedure described in Example 1 yields 28.2 g of product as an oil, boiling point 162°–167° C. at 0.4–0.5 mm. of Hg.

(B)

3,3-Dichloro-1-[3-(dimethylamino)propyl]-4-(3,4,5-trimethoxyphenyl)-2-azetidinone, hydrochloride (1:1)

N,N-Dimethyl-N'-[(3,4,5-trimethoxyphenyl)methylene]-1,3-propanediamine (14 g) and 21 g of trichloroacetic anhydride are reacted in 95 ml. of xylene following the procedure described in Example 1. (Final heating for 20 minutes on steam bath) to give 13.8 g of solid base, melting point 108°–110° C. (sintering at 104° C.). Crystallization (of 13.3 g) from 65 ml of hot benzene-65 ml hexane (some tarry material which initially separates removed by filtration) gives 9.3 g of the free base of the title compound, melting point 113°–115° C.

The base (9.2 g) is dissolved in dichloromethane, treated with 4.4 ml. of 5.6 N alcoholic hydrogen chloride, and the solvents are removed on a rotary evaporator to give a foamy residue which is taken up in 40 ml. of acetonitrile and diluted to 250 ml. with ether. On seeding and rubbing, the crystalline hydrochloride salt separates, yielding after 3 days in the cold, 9.3 g of material; melting point 172°–174° C. Following recrystallization from 30 ml. of warm acetonitrile-90 ml. ethyl acetate, the title compound weighs 8.4 g, melting point 173°–175° C.

EXAMPLE 7

3,3-Dichloro-1-[3-(dimethylamino)propyl]-4-[3-(trifluoromethyl)phenyl]-2-azetidinone, hydrochloride (1:1)

(A)

N,N-Dimethyl-N'-(3-trifluoromethylbenzylidene)-propanediamine

Ten grams of m-trifluoromethylbenzaldehyde and 5.9 g of 3-dimethylaminopropylamine are reacted in 40 ml. of benzene following the procedure described in Example 1 to give 13.3 g of oily product, boiling point 92°–95° C. at 0.5 mm. of Hg.

(B)

3,3-Dichloro-1-[3-(dimethylaminopropyl]-4-[3-(trifluoromethyl)phenyl]-2-azetidinone, hydrochloride N,N-Dimethyl-N'-(3-trifluoromethylbenzylidine)-propanediamine (12.8 g) and 21 g of trichloroacetic anhydride are reacted in 95 ml. of xylene following the procedure described in Example 1. Carbon dioxide evolution begins at about 60° C. and becomes quite vigorous at 85° C. Darkening occurs at 93° C. as a solid separates. After heating on the steam bath (90°–93° C.) for 0.5 hours, the mixture is worked up following the procedure described in Example 1 to give 7.1 g of crude base as an oil. The latter is dissolved in dichloromethane, treated with 1 equivalent of alcoholic hydrogen chloride, and the solvents are removed on a rotary evaporator. When the foamy residue is taken up in 40 ml. of acetonitrile and diluted to 400 ml. with ether, no crystallization takes place on rubbing and standing in the cold. The solvents are evaporated and the residue slowly solidifies when covered with ether, rubbed, and cooled for 3 days; crude yield, 7.0 g, melting point 110°–114° C. (sintering at 107° C). Crystallization from 20 ml. of isopropanol-80 ml. of ether, initially at room temperature and then finally in the cold room, gives 4.6 g of the title compound, melting point 115°–117° C. (sintering at 112° C.).

EXAMPLE 8

3,3-Dichloro-1-[3-(dimethylamino)propyl]-4-(2-naphthalenyl)-2-azetidinone, hydrochloride (1:1)

(A)

N,N-Dimethyl-N'-(2-naphthalenylmethylene)-1,3-propanediamine

Interaction of 15.6 g of 2-naphthaldehyde and 10.2 g of 3-dimethylaminopropylamine in 80 ml. of benzene following the procedure described in Example 1 yields 22.4 g of oily product; boiling point 146°–149° C. at 0.1–0.2 mm. of Hg. The material solidifies when stored in the cold, melting point 29°–31° C.

(B)
3,3-Dichloro-1-[3-(dimethylamino)propyl]-4-(2-naphthalenyl)-2-azetidinone, hydrochloride (1:1)

N,N-Dimethyl-N'-(2-naphthalenylmethylene)-1,3-propanediamine (11 g) and 19.7 g of trichloroacetic anhydride are reacted in 90 ml. of xylene following the procedure described in Example 1 (final heating period 20 minutes on steam bath) to give 11.5 g of crude base as an oil. The oil is dissolved in dichloromethane, treated with 6 ml. of 5.6 N alcoholic hydrogen chloride, and the solvents are removed on a rotary evaporator; the solid residue weighs 12 g, melting point 183°–185° C. Crystallization from 80 ml. of acetonitrile gives 9.1 g of solid; melting point 199°–201° C. Recrystallization from 125 ml. of acetonitrile yields 7.3 g of the title compound, melting point 200°–202° C.

EXAMPLE 9

4-(1,3-Benzodioxol-5-yl)-3,3-dichloro-1-[3-(dimethylamino)propyl]-2-azetidinone, hydrochloride (1:1)

(A)
N,N-Dimethyl-N'-(3,4-methylenedioxybenzylidene)-1,3-propanediamine

Interaction of 50 g of piperonal and 34 g of 3-dimethylaminopropylamine in 240 ml. of benzene following the procedure described in Example 1 yields 58.6 g of the product as an oil, boiling point 131°–136° C. at 0.2–0.3 mm. of Hg.

(B)
4-(1,3-Benzodioxol-5-yl)-3,3-dichloro-1-[3-(dimethylamino)propyl]-2-azetidinone, hydrochloride (1:1)

N,N-Dimethyl-N'-(3,4-methylenedioxybenzylidene)-1,3-propanediamine (11.7 g) and 21 g of trichloroacetic anhydride are reacted in 95 ml. of xylene following the procedure described in Example 1 (final 20 minutes heating period on steam bath) to give 13.7 g of oily base. The hydrochloride salt (prepared in dichloromethane, evaporated, and the almost completely solid residue crystallized from 60 ml. warm acetonitrile-60 ml. ether) weighs 11.9 g, melting point 175°–177° C. (sintering at 172° C.). Recrystallization from 40 ml. of hot acetonitrile-100 ml. ethyl acetate yields 10.6 g of the title compound, melting point 175°–177° C. (sintering at 172° C.).

EXAMPLE 10

3,3-Dichloro-4-(4-chlorophenyl)-1-[2-(4-morpholinyl)ethyl]-2-azetidinone, hydrochloride (1:1)

(A)
N-(4-Chlorobenzylidene)-4-(2-aminoethyl)morpholine

Interaction of 50 g of N-(2-aminoethyl)morpholine and 54 g of p-chlorobenzaldehyde in 130 ml. of benzene following the procedure described in Example 1 yields 81.8 g of an oily product, boiling point 139°–145° C. at 0.05–0.1 mm. of Hg. The material crystallizes on storing in the cold.

(B)
3,3-Dichloro-4-(4-chlorophenyl)-1-[2-(4-morpholinyl)ethyl]-2-azetidinone, hydrochloride (1:1)

A stirred solution of 17 g of N-(4-chlorobenzylidene)-4-(2-aminoethyl)morpholine in 100 ml. of dioxane is treated dropwise at 13°–15° C. with 28 g of trichloroacetic anhydride dissolved in 60 ml. of dioxane. After the addition, the solution is heated by means of a mantle while passing in nitrogen. Cloudiness occurs at approximately 55° C. and at 62°–67° C. the mixture becomes dark as carbon dioxide is evolved and some tarry material separates. The mantle is replaced with a steam bath and heating and stirring are continued for 0.5 hours. At the end of this period carbon dioxide evolution has essentially ceased. The mixture is cooled and worked up as described in Example 1 to give 19 g of crude base as an oil. Crystallization from a boiling mixture of 80 ml. of isopropyl ether and 30 ml. of hexane yields 11.8 g of the free base of the title compound, melting point 72°–74° C.

The base (11.6 g) is dissolved in 60 ml. of acetonitrile, cooled, treated with 6 ml. of 5.5 N alcoholic hydrogen chloride, and diluted to 300 ml. with ether. On rubbing, the crystalline hydrochloride salt separates, yielding, after cooling for about 16 hours, 12.3 g of material, melting point 210°–212° C. Crystallization from 150 ml. of hot acetonitrile-300 ml. of ethyl acetate yields 10.6 g of the title compound, melting point 210°–212° C.

EXAMPLES 11–14

Following the procedure of Example 1, but substituting the compound listed in column I for benzaldehyde and the compound listed in column II for N,N-dimethylpropanediamine, yields the hydrochloride salt of the compound listed in column III.

|    | Column I | Column II | Column III |
| --- | --- | --- | --- |
| 11 | N-(4-aminobutyl)pyrrolidine | 3,4-dichlorobenzaldehyde | 3,3-dichloro-4-(3,4-dichlorophenyl)-1-[4-(1-pyrrolidinyl)butyl]-2-azetidinone |
| 12 | N-(2-aminoethyl)piperidine | 3-fluoro-4-methoxybenzaldehyde | 3,3-dichloro-4-(3-fluoro-4-methoxyphenyl)-1-[2-(1-piperidinyl)ethyl]-2-azetidinone |
| 13 | N-(3-aminopropyl)piperazine | 2-methylbenzaldehyde | 3,3-dichloro-4-(2-methylphenyl)-1-[3-(1-piperazinyl)propyl]-2-azetidinone |
| 14 | N-(4-aminobutyl)-4-methylpiperazine | 3-nitrobenzaldehyde | 3,3-dichloro-1-[4-(4-methyl-1-piperazinyl)butyl]-4-(3-nitrophenyl)-2-azetidinone |

What is claimed is:
1. A compound having the formula

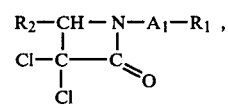

or a pharmaceutically acceptable salt thereof, wherein $R_1$ is dialkylamino, 1-pyrrolidinyl, 1-piperidinyl, 4-morpholinyl, 1-piperazinyl, or 4-alkyl-1-piperazinyl; $R_2$ is phenyl, phenyl monosubstituted with an alkyl, trifluoromethyl or nitro group, phenyl mono-, di- or trisubstituted with halogen or alkoxy groups, 1-naphthyl, 2-naphthyl, or 1,3-benzodioxol-5-yl; $A_1$ is an alkylene group having 2 to 4 carbon atoms; and wherein the terms "alkyl" and "alkoxy" refer to groups having 1 to 6 carbon atoms.

2. A compound in accordance with claim 1 wherein $R_1$ is dialkylamino.

3. A compound in accordance with claim 1 wherein $R_1$ is 1-pyrrolidinyl, 1-piperidinyl, 4-morpholinyl, 1-piperazinyl, or 4-alkyl-1-piperazinyl.

4. A compound in accordance with claim 1 wherein $R_2$ is phenyl.

5. A compound in accordance with claim 1 wherein $R_2$ is 2-methoxyphenyl.

6. A compound in accordance with claim 1 wherein $R_2$ is 3,4,5-trimethoxyphenyl.

7. A compound in accordance with claim 1 wherein $R_2$ is 3-(trifluoromethyl)phenyl.

8. A compound in accordance with claim 1 wherein $R_2$ is 2-naphthyl.

9. A compound in accordance with claim 1 wherein $R_2$ is 1,3-benzodioxol-5-yl.

10. The compound in accordance with claim 1, 3,3-dichloro-1-[3-(dimethylamino)propyl]-4-phenyl-2-azetidinone, hydrochloride (1:1).

11. The compound in accordance with claim 1, 3,3-dichloro-1-[2-(dimethylamino)ethyl]-4-phenyl-2-azetidinone, hydrochloride (1:1).

12. The compound in accordance with claim 1, 3,3-dichloro-1-[3-(4-morpholinyl)propyl]-4-phenyl-2-azetidinone, hydrochloride (1:1).

13. The compound in accordance with claim 1, 3,3-dichloro-1-[2-(4-morpholinyl)ethyl]-4-phenyl-2-azetidinone, hydrochloride (1:1).

14. The compound in accordance with claim 1, 3,3-dichloro-1-[3-(dimethylamino)propyl]-4-(2-methoxyphenyl)-2-azetidinone, hydrochloride (1:1).

15. The compound in accordance with claim 1, 3,3-dichloro-1-[3-(dimethylamino)propyl]-4-(3,4,5-trimethoxyphenyl)-2-azetidinone, hydrochloride (1:1).

16. The compound in accordance with claim 1, 3,3-dichloro-1-[3-(dimethylamino)propyl]-4-[3-(trifluoromethyl)phenyl]-2-azetidinone, hydrochloride (1:1).

17. The compound in accordance with claim 1, 3,3-dichloro-1-[3-(dimethylamino)propyl]-4-(2-naphthalenyl)-2-azetidinone, hydrochloride (1:1).

18. The compound in accordance with claim 1, 4-(1,3-benzodioxol-5-yl)-3,3-dichloro-1-[3-(dimethylamino)propyl]-2-azetidinone, hydrochloride (1:1).

19. The compound in accordance with claim 1, 3,3-dichloro-4-(4-chlorophenyl)-1-[2-(4-morpholinyl)ethyl]-2-azetidinone, hydrochloride (1:1).

* * * * *